| United States Patent [19] | | [11] | 4,180,394 |
|---|---|---|---|
| Franz et al. | | [45] | Dec. 25, 1979 |

[54] DERIVATIVES OF N-TRIFLUOROACETYL-N-PHOSPHONOMETHYLGLYCINATES AND THE HERBICIDAL USE THEREOF

[75] Inventors: John E. Franz, Crestwood; Robert J. Kaufman, University City, both of Mo.

[73] Assignee: Monsanto Company, St. Louis, Mo.

[21] Appl. No.: 922,930

[22] Filed: Jul. 10, 1978

[51] Int. Cl.$^2$ ............................ A01N 9/36; C07F 9/40; C07F 9/44

[52] U.S. Cl. ................................ 71/86; 71/87; 260/940; 260/944; 560/17; 560/41; 560/147; 560/155; 560/169; 560/172; 544/130; 544/157; 546/22

[58] Field of Search .............. 260/293.73, 293.76, 260/293.85, 293.86, 944; 71/86, 87; 560/17, 41, 147, 155, 169, 172; 544/130, 157; 546/22

[56] References Cited

U.S. PATENT DOCUMENTS

| 3,799,758 | 3/1974 | Franz | 71/86 |
|---|---|---|---|
| 3,835,000 | 9/1974 | Frazier et al. | 71/86 UX |
| 3,853,530 | 12/1974 | Franz | 71/86 X |
| 3,933,946 | 1/1976 | Gaertner | 260/944 |
| 3,970,695 | 12/1974 | Rueppel | 71/86 X |
| 4,047,926 | 9/1977 | Rueppel | 71/86 |
| 4,053,505 | 10/1977 | Dutra | 260/970 X |
| 4,062,669 | 12/1977 | Franz | 71/86 |

FOREIGN PATENT DOCUMENTS 849907 6/1977 Belgium .

OTHER PUBLICATIONS

Rueppel, et al., Biomedical Mass Spectrometry, 3 (1976), pp. 28–31.

*Primary Examiner*—Joseph P. Brust
*Attorney, Agent, or Firm*—William T. Black; Donald W. Peterson

[57] ABSTRACT

This disclosure relates to derivatives of N-trifluoroacetyl-N-phosphonomethylglycinates wherein different moieties are attached to the phosphorus atom, to herbicidal compositions containing same and to the herbicidal use thereof.

27 Claims, No Drawings

DERIVATIVES OF N-TRIFLUOROACETYL-N-PHOSPHONOMETHYLGLYCINATES AND THE HERBICIDAL USE THEREOF

This invention relates to derivatives of N-trifluoroacetyl-N-phosphonomethylglycinates, to herbicidal compositions containing same and to the herbicidal use thereof. More particularly, this invention relates to alkyl-N-trifluoroacetyl-N-phosphonomethylglycinates wherein different moieties are bonded to the phosphorus atom.

In accordance with U.S. Pat. No. 3,970,695, issued July 20, 1976, N-perfluoroacyl-N-phosphonomethylglycines of the formula

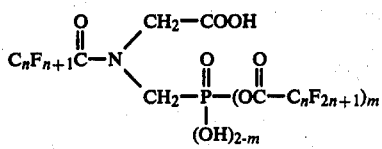

wherein n is an integer of from 1 to 4 and m is 1 or 0 are produced by reacting a perfluoroacyl anhydride with N-phosphonomethylglycine in the presence of a perfluoroalkanoic acid to form the compound of the formula wherein m is 1 and then by hydrolysis to form the compounds wherein m is 0.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530. The production of triesters of N-phosphonomethylglycine is disclosed in U.S. Pat. Nos. 4,053,505 and 3,835,000 and in Belgian Pat. No. 849,907.

Ester derivatives of N-trifluoroacetyl-N-phosphonomethylglycine wherein the ester groups attached to phosphorus and to the carboxyl group are all the same and are alkyl groups as disclosed by Rueppel et al, *Biomedical Mass Spectrometry*, Volume 3 (1976), pages 28–31. These compounds were prepared by preparing the N-trifluoroacetyl derivative of U.S. Pat. No. 3,970,695 and then reacting it with diazobutane in n-butanol.

The novel N-trifluoroacetyl-N-phosphonomethylglycinates of this invention are those having the formula

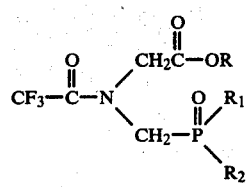

wherein R is an alkyl group of from 1 to 10 carbon atoms or chlorinated lower alkyl group, $R_1$ is a member of the group consisting of lower alkoxy, lower alkylthio, phenoxy, phenylthio, substituted phenoxy, substituted phenylthio, lower alkylamino, lower dialkylamino, morpholino and N-piperidinoamino and $R_2$ is a member of the group consisting of lower alkylthio, phenoxy, phenylthio, substituted phenoxy, substituted phenylthio, lower alkylamino, lower dialkylamino, lower alkenylamino, lower dialkenylamino, lower alkynylamino, lower dialkynylamino, morpholino and N-piperidinoamino with the proviso that $R_1$ and $R_2$ cannot represent the same group.

As employed herein, the terms "lower alkyl", "lower alkenyl", "lower alkynyl", "lower alkoxy" and "lower alkylthio" designate those radicals containing up to six carbon atoms in a straight or branched chain.

As employed herein, the term "halo" includes chloro, bromo, iodo and fluoro. Preferably, the halo groups are bromo, chloro or fluoro.

Illustrative of the substituted phenoxy or phenylthio groups which $R_1$ and $R_2$ represent are monosubstituted phenylthio or phenoxy groups wherein the substituent is in the ortho, meta or para position, for example, chlorophenoxy, bromophenoxy, fluorophenylthio, cyanophenylthio, nitrophenylthio and trifluoromethylphenoxy and the disubstituted phenylthio or phenoxy groups wherein the substituents are the same or different and are located in the 2, 3, 4, 5 or 6 positions of the phenyl ring, for example, dichlorophenoxy, dibromophenylthio, chlorocyanophenoxy, dicyanophenoxy, dinitrophenoxy, bromonitrophenylthio, chlorotrifluoromethylphenoxy and the like.

Illustrative of the alkyl groups represented by R are, for example, methyl, ethyl, propyl, hexyl, cyclohexyl, decyl and their isomers. Preferably, R is a lower alkyl group, i.e., an alkyl group containing from 1 to 6 carbon atoms.

The novel compounds of this invention are produced by reacting an ester dichloride of N-trifluoroacetyl-N-phosphonomethylglycine having the formula

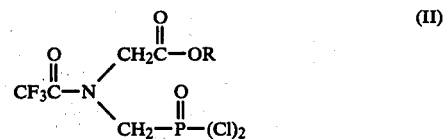

wherein R is as above-defined in a stepwise manner with nucleophiles $R_1$—H or $R_2$—H wherein $R_1$ and $R_2$ are as above-defined in an organic solvent and in the presence of a tertiary amine hydrogen chloride acceptor under essentially anhydrous conditions at a temperature of from about 10° C. to about 50° C. preferably at ambient temperatures.

In producing the compounds of this invention by the above reaction, the tertiary amine hydrogen chloride acceptor is preferably used in excess of stoichiometric to insure completeness of reaction. By the term "tertiary amine hydrogen chloride acceptor" as employed herein is meant tertiary alkylamines such as trimethylamine, triethylamine, tributylamine, trihexylamine and the like as well as aromatic tertiary amines such as pyridine, quinoline and the like.

The ratio of the reactants must be controlled in each step. It is, of course, apparent to those skilled in the art that each chlorine atom in the N-trifluoroacetyl-N-phosphonomethylglycinyl dichloride will react with one nucleophile ($R_1$—H or $R_2$—H) and that, therefore, one would employ in each step one equivalent of the nucleophile reactant per one mole of the dichloride reactant. The nucleophiles are added in a stepwise manner with stirring to insure intimate contact with the dichloride reagent allowing sufficient time between the stepwise additions to insure complete reaction of the first nucleophile before the addition of the second nucleophile. Otherwise, one obtains a mixture of products from which it is very difficult to separate the compounds of this invention.

The ester dichlorides of Formula II employed as a reactant in producing the compounds of this invention are prepared by reacting an ester of N-phosphonomethylglycine of the formula

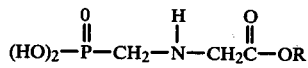

wherein R has the above-defined meaning with trifluoroacetic acid anhydride at temperatures of from about 10° C. to about 35° C., removing any excess anhydride and then treating the reaction product with excess thionyl chloride under refluxing conditions. The excess thionyl chloride is removed under vacuum to yield the dichlorides of Formula II.

The compounds of this invention are useful as herbicides.

The following non-limiting examples will serve to demonstrate to those skilled in the art the manner in which specific compounds within the scope of this invention can be prepared.

EXAMPLE 1

Ethyl N-trifluoroacetyl-N-(dichlorophosphonomethyl)glycinate (3.96 g, 0.012 mole) was dissolved in 50 ml. of ether and added dropwise to a solution of diethylamine (2.89 g, 0.0396 mole) in 50 ml. of ether. After 30 minutes, phenol (1.13 g, 0.012 mole) in 50 ml. of ether was added over a 10-minute period. The resulting mixture was stirred overnight at room temperature and then filtered. The filtrate was washed twice with 50 ml. portions of 3% ammonium hydroxide, dried over magnesium sulfate and concentrated in vacuo to yield ethyl N-trifluoroacetyl-N-((N',N'-diethylamino) (phenoxy)-phosphonomethyl)glycinate as a clear oil (3.15 g), $N_D^{27}=1.4671$.

Anal. Calc'd: C, 48.12; H, 5.70; N, 6.60. Found: C, 48.26; H, 5.67; N, 6.54.

EXAMPLE 2

A solution of ethyl N-trifluoroacetyl-N-(dichlorophosphonomethyl)glycinate (3.63 g, 0.011 mole) in 50 ml. of benzene was treated with a solution of N-methylaniline (2.46 g, 0.023 mole) and triethylamine (2.3 g, 0.023 mole) in 40 ml. of benzene. The resulting mixture was refluxed for 5 hours, then cooled to 25° C. and treated with phenol (1.03 g, 0.011 mole) for three hours. The reaction mixture was filtered and concentrated in vacuo. The residue was extracted into petroleum ether and the petroleum ether solution was washed with 50 ml. of 3% aqueous ammonium hydroxide and 50 ml. of 5% aqueous hydrochloric acid. After drying over magnesium sulfate, the solution was concentrated to yield ethyl N-trifluoroacetyl-N-((N'-methylanilino)(phenoxy)phosphonomethyl)glycinate as a golden oil (4.6 g), $N_D^{27}=1.5087$.

Anal. Calc'd: C, 52.41; H, 4.84; N, 6.11; P, 6.76. Found: C, 52.19; H, 4.86; N, 6.12; P, 6.66.

EXAMPLE 3

Ethyl N-trifluoroacetyl-N-(dichlorophosphonomethyl)glycinate (6.6 g, 0.02 mole) was dissolved in 100 ml. of ether, cooled to 0° C. and treated with a solution of methanol (0.8 g, 0.02 mole) and triethylamine (2.78 g, 0.02 mole) in 50 ml. of ether. After two hours, the solution was filtered and the filtrate cooled to 0° C. and treated with a solution of thiophenol (2.05 ml, 0.02 mole) and triethylamine (2.78 ml, 0.02 mole) in 50 ml. of ether. After two hours, the solution was filtered and the filtrate was concentrated in vacuo. The residue was extracted into petroleum ether and the petroleum ether was removed by distillation in vacuo. The residue (1.5 g) was chromatographed on silica gel eluting with ether/benzene (7/3) to afford ethyl N-trifluoroacetyl-N-(methoxy(phenylthio)phosphonomethyl)glycinate as a colorless oil (1 g), $N_D=1.5047$.

Anal. Calc'd: C, 42.11; H, 4.29; P, 7.76. Found: C, 42.50; H, 4.54; P, 7.71.

EXAMPLE 4

A solution of ethyl N-trifluoroacetyl-N-(dichlorophosphonomethyl)glycinate (8.25 g, 0.025 mole) in 100 ml. of ether was cooled to 0° C. and treated with a solution of methanol (1.01 ml, 0.025 mole) and triethylamine (3.49 ml, 0.025 mole) in 100 ml. of ether. After two hours, the mixture was filtered and the filtrate was cooled to 0° C. and treated with a solution of m-chlorophenol (3.21 g, 0.025 mole) and triethylamine (3.49 ml, 0.025 mole) in 100 ml. of ether. The resulting solution was stirred overnight at 25° C., filtered and the filtrate concentrated in vacuo. The residue was extracted into petroleum ether and the resulting solution was concentrated in vacuo to yield ethyl N-trifluoroacetyl-N-(methoxy(m-chlorophenoxy)phosphonomethyl)glycinate as a yellow oil (7.55 g), $N_D=1.4803$.

Anal. Calc'd: C, 40.26; H, 3.86; P, 7.42. Found: C, 40.22; H, 3.81; P, 7.41.

EXAMPLE 5

A solution of N-trifluoroacetyl-N-(dichlorophosphonomethyl)glycinate (8.25 g, 0.025 mole) in 100 ml. of ether was cooled to 0° C. and a solution of methanol (1.01 ml, 0.025 mole) and triethylamine (3.49 ml, 0.025 mole) in 30 ml. of ether was added. After two hours, the reaction mixture was filtered and the filtrate was cooled to 0° C. and treated with methanethiol (1.38 ml, 0.025 mole) and triethylamine (3.49 ml, 0.025 mole). This mixture was stirred overnight, then concentrated in vacuo to afford an oil which was chromatographed on silica gel. The column was eluted with methylene chloride/ethyl acetate to yield ethyl N-trifluoroacetyl-N-(methoxy(methylthio)phosphonomethyl)glycinate (2.3 g) as an oil, $N_D=1.4571$.

Anal. Calc'd: C, 32.05; H, 4.48; P, 9.18. Found: C, 32.16; H, 4.53; P, 9.07.

EXAMPLE 6

A solution of ethyl N-trifluoroacetyl-N-(dichlorophosphonomethyl)glycinate (8.25 g, 0.025 mole) in 150 ml. of ether was cooled to 0° C. and treated with a solution of methanol (1.01 ml, 0.025 mole) and triethylamine (3.49 ml, 0.025 mole) in 25 ml. of ether. The solution was stirred for two hours, then filtered and the filtrate was cooled and treated with isopropylamine (4.25 ml. 0.05 mole) in 100 ml. of ether. After stirring for 16 hours, the mixture was filtered and the filtrate was washed with water, dried over sodium sulfate and concentrated in vacuo to yield ethyl N-trifluoroacetyl-N-(methoxy(isopropylamino)phosphonomethyl)glycinate (6.1 g) as a yellow oil, $N_D=1.4335$.

Anal. Calc'd: C, 37.94; H, 5.79; P, 8.89. Found: C, 37.91; H, 5.95; P, 8.96.

EXAMPLE 7

A solution of ethyl N-trifluoroacetyl-N-(dichlorophosphonomethyl)glycinate (8.25 g, 0.025 mole) in ether (150 ml.) was cooled to 0° C. and a solution of phenol (2.35 g, 0.025 mole) and triethylamine (3.49 ml, 0.025 mole) in 50 ml. of ether was added to it. The resulting mixture was stirred for three hours, then filtered. The filtrate was cooled to 0° C. and thiophenol (2.5 ml, 0.025 mole) and triethylamine (3.49 ml, 0.025 mole) in 50 ml. of ether was added. The resulting solution was stirred overnight at 25° C., filtered and concentrated in vacuo. The residue was chromatographed on silica eluting first with methylene chloride, then with ether to yield ethyl N-trifluoroacetyl-N-(phenoxy(phenylthio)phosphonomethyl)glycinate (7.97 g) as a white solid, m.p. 80°-82° C.

Anal. Calc'd: C, 49.46; H, 4.15; P, 6.71. Found: C, 49.49; H, 4.30; P, 6.87.

EXAMPLE 8

A solution of phenol (2.3 g, 0.025 mole) and triethylamine (3.49 ml, 0.025 mole) in 50 ml. of ether was added to a solution of ethyl N-trifluoroacetyl-N-(dichlorophosphonomethyl)glycinate (8.25 g, 0.025 mole) in 150 ml. of ether. The resulting solution was filtered and the filtrate was cooled to 0° C. and treated with isopropylamine (4.2 ml, 0.05 mole) in 50 ml. of ether. After stirring overnight at 25° C., the reaction mixture was filtered, washed with water, dried over sodium sulfate and concentrated in vacuo to afford a gummy solid. This solid was triturated with petroleum ether to give ethyl N-trifluoroacetyl-N-(phenoxy(N'-isopropylamino)phosphonomethyl)glycinate (5.25 g) as a white solid, m.p. 80°-82° C.

Anal. Calc'd: C, 46.83; H, 5.40; N, 6.83. Found: C, 46.62; H, 5.39; N, 6.80.

EXAMPLE 9

A solution of methanol (1.01 ml, 0.025 mole) and triethylamine (3.49 ml, 0.025 mole) in 50 ml. of ether was added to a solution of ethyl N-trifluoroacetyl-N-(dichlorophosphonomethyl)glycinate (8.23 g, 0.025 mole) in 150 ml. of ether at 0° C. The mixture was stirred for two hours, then filtered. The filtrate was cooled to 0° C. and treated with N-aminopiperidine (5.2 ml, 0.05 mole) in 50 ml. of ether. After stirring overnight, the reaction mixture was filtered, washed with 25 ml. water, dried over sodium sulfate and concentrated in vacuo. The residual oil was filtered through florosil in methylene chloride and concentrated in vacuo to give ethyl N-trifluoroacetyl-N-(methoxy(N'-piperidinoamino)phosphonomethyl)glycinate (0.9 g) as a light yellow oil, $N_D^{22}=1.4516$.

Anal. Calc'd (.½H₂O): C, 39.16; H, 6.02; N, 10.54. Found: C, 39.30; H, 5.98; N, 10.03.

EXAMPLE 10

A solution of ethyl N-trifluoroacetyl-N-(dichlorophosphonomethyl)glycinate (8.25 g, 0.025 mole) in tetrahydrofuran (THF) (150 ml) was added to N-methylaniline (5.3 ml, 0.05 mole) in THF at 60° C. After 24 hours, the solution was cooled to 25° C. and filtered and the filtrate was treated with a solution of methanol (1.01 ml, 0.025 mole) and triethylamine (3.49 ml, 0.025 mole) in 50 ml. of THF. After stirring overnight, the solution was filtered and the filtrate was concentrated in vacuo. The oily residue was chromatographed on florosil eluting with methylene chloride. The eluted solution was washed with 10% hydrochloric acid, saturated aqueous sodium chloride, 3% ammonium hydroxide and finally saturated aqueous sodium chloride. The solution was dried over sodium sulfate and concentrated in vacuo to yield ethyl N-trifluoroacetyl-N-(methoxy(N'-methylanilino)phosphonomethyl)glycinate (4.0 g) as a yellow oil, $N_D=1.4862$.

Anal. Calc'd (.½H₂O): C, 44.41; H, 5.18; N, 6.91. Found: C, 44.10; H, 4.91; N, 7.02.

EXAMPLE 11

A solution of isopropanol (1.9 ml, 0.025 mole) and triethylamine (3.49 ml, 0.025 mole) in 50 ml. of ether was added to ethyl N-trifluoroacetyl-N-(dichlorophosphonomethyl)glycinate (8.25 g, 0.025 mole) in 150 ml. of ether at 0° C. After three hours, the solution was filtered and the filtrate was cooled to 0° C., treated with a solution of isopropylamine (4.2 ml, 0.05 mole) in 50 ml. of ether. The resulting mixture was stirred overnight at 25° C., then filtered. The filtrate was washed with 3% aqueous hydrochloric acid, saturated sodium chloride solution, 3% ammonium hydroxide and saturated sodium chloride. The filtrate was dried over sodium sulfate and concentrated in vacuo to afford ethyl N-trifluoroacetyl-N-(isopropyl(N'-isopropylamino)phosphonomethyl)glycinate (4.0 g) as a white solid, m.p. 85°-88° C.

Anal. Calc'd: C, 41.49; H, 6.43; N, 7.44. Found: C, 41.34; H, 6.45; N, 7.39.

EXAMPLE 12

A solution of thiophenol (2.9 ml, 0.0285 mole) and triethylamine (3.97 ml) in 50 ml. of ether was added to a solution of ethyl N-trifluoroacetyl-N-(dichlorophosphonomethyl)glycinate (9.9 g, 0.03 mole) in 150 ml. of ether at 0° C. After three hours, the solution was filtered and the cooled (0° C.) filtrate was treated with a solution of isopropylamine (4.85 ml, 0.057 mole) in 50 ml. of ether. After stirring overnight, the solution was filtered, washed with 1.5% aqueous hydrochloric acid, 1.5% ammonium hydroxide and saturated aqueous sodium chloride. Concentration in vacuo afforded an oil which was chromatographed on silica gel eluting with ethyl acetate-cyclohexane (1:1) to yield ethyl N-trifluoroacetyl-N-(phenylthio(isopropylamino)phosphonomethyl)glycinate (1.75 g) as a white solid, m.p. 102°-103° C.

Anal. Calc'd: C, 45.07; H, 5.20; N, 6.57. Found: C, 44.87; H, 5.22; N, 6.50.

EXAMPLE 13

A solution of phenol (2.3 g, 0.025 mole) and triethylamine (3.49 ml, 0.025 mole) in 50 ml. of ether was added to a solution of ethyl N-trifluoroacetyl-N-(dichlorophosphonomethyl)glycinate (8.25 g, 0.025 mole) in 150 ml. of ether at 0° C. After two hours, the solution was filtered and the filtrate was added to a cooled (0° C.) solution of N-aminopiperidine (5.2 ml, 0.05 mole) in 100 ml. of ether. The resulting solution was stirred at 25° C. for 16 hours, then filtered. The filtrate was washed with 0.3% hydrochloric acid, dried over sodium sulfate and concentrated in vacuo to afford ethyl N-trifluoroacetyl- N-(phenoxy(N-piperidinoamino)phosphonomethyl)-glycinate which could not be further purified by any means.

EXAMPLE 14

A solution of isopropanol (1.0 ml, 0.025 mole) and triethylamine (3.5 ml, 0.025 mole) in 50 ml. of tetrahydrofuran was added to a solution of β-chloroethyl N-trifluoroacetyl-N-(dichlorophosphonomethyl)glycinate (9.1 g, 0.025 mole) in 250 ml. of ether at 0° C. After three hours, the mixture was filtered and the filtrate was added to a cooled (0° C.) solution of isopropylamine (4.2 ml, 0.05 mole) in 50 ml. of tetrahydrofuran. After stirring for 16 hours at 25° C., the reaction mixture was filtered and the filtrate was concentrated in vacuo. The residual oil was dissolved in methylene chloride and washed with 3% hydrochloric acid, 3% ammonium hydroxide and saturated sodium chloride solution. The solution was dried over sodium sulfate and concentrated in vacuo to yield a solid. Recrystallization from ethyl acetate-hexane (1:10) yielded β-chloroethyl N-trifluoroacetyl-N-(isopropyl(isopropylamino)phosphonomethyl)glycinate as a white solid, m.p. 87.5°–89° C.

Anal. Calc'd: C, 38.01; H, 5.64; N, 6.82. Found: C, 38.00; H, 5.65; N, 6.82.

EXAMPLE 15

A solution of isopropanol (2.9 ml, 0.038 mole) and triethylamine (5.3 ml, 0.038 mole) in 50 ml. of ether was added to a solution of ethyl N-trifluoroacetyl-N-(dichlorophosphonomethyl)glycinate (13.2 g, 0.04 mole) in 150 ml. of ether at 0° C. After three hours, the solution was filtered and the cooled (0° C.) filtrate was treated with a solution of thiophenol (3.9 ml, 0.038 mole) and triethylamine (5.3 ml, 0.038 mole) in 50 ml. of ether. The resulting mixture was stirred at 25° C. for 16 hours, then filtered. The filtrate was washed with 3% hydrochloric acid, 3% ammonium hydroxide and saturated sodium chloride solution, then concentrated in vacuo. The residual oil was chromatographed on silica gel eluting with ethyl acetate/cyclohexane (6:4) to afford ethyl N-trifluoroacetyl-N-(isopropoxy(phenylthio)phosphonomethyl)glycinate (7.7 g) as a light yellow oil, $N_D^{25} = 1.4951$.

Anal. Calc'd: C, 44.97; H, 4.95; N, 3.28; S, 7.50. Found: C, 44.88; H, 4.97; N, 3.27; S, 7.45.

EXAMPLE 16

A solution of diethylamine (5.0 ml, 0.05 mole) in 50 ml. of ether was added to a solution of ethyl N-trifluoroacetyl-N-(dichlorophosphonomethyl)glycinate (8.25 g, 0.025 mole) in 150 ml. of ether at 0° C. The solution was stirred for two hours, then filtered and the filtrate treated with a solution of thiophenol (2.4 ml, 0.025 mole) and triethylamine (3.4 ml, 0.025 mole) in 50 ml. of ether at 0° C. After stirring overnight, the solution was filtered and the filtrate was washed with 0.3% aqueous hydrochloric acid, dried over sodium sulfate and concentrated in vacuo to yield ethyl N-trifluoroacetyl-N-(diethylamino(phenylthio)phosphonomethyl)-glycinate (8.7 g) as a yellow oil, $N_D^{22} = 1.5049$.

EXAMPLE 17

A solution of ethanethiol (2.13 ml, 0.0285 mole) and triethylamine (3.97 ml, 0.0285 mole) in 50 ml. of ether was added to a solution of ethyl N-trifluoroacetyl-N-(dichlorophosphonomethyl)glycine (9.9 g, 0.03 mole) in 150 ml. of ether at 0° C. The resulting mixture was stirred for three hours, then filtered and the cooled (0° C.) filtrate was treated with a solution of isopropylamine (4.85 ml, 0.057 mole) in 50 ml. of ether. After stirring overnight, the reaction mixture was filtered and washed with 1.5% hydrochloric acid, 1.5% ammonium hydroxide and saturated aqueous sodium chloride. The resulting solution was concentrated in vacuo to afford an oil which was recrystallized from ethyl acetate-cyclohexane (1:5) to give ethyl N-trifluoroacetyl-N-(isopropylamino(ethylthio)phosphonomethyl)glycinate as a white solid, m.p. 85°–87° C.

Anal. Calc'd (.½H₂O): C, 37.17; H, 5.93; N, 7.22; S, 8.28. Found: C, 37.20; H, 6.01; N, 7.23; S, 8.31.

EXAMPLE 18

A solution of phenol (2.68 g, 0.0285 mole) and triethylamine (3.97 ml, 0.0285 mole) in 50 ml. of ether was added to a solution of ethyl N-trifluoroacetyl-N-(dichlorophosphonomethyl)glycinate (9.9 g, 0.03 mole) in 175 ml. of ether at 0° C. After three hours, the reaction mixture was filtered and the cooled (0° C.) filtrate was treated with a solution of ethanethiol (2.13 ml, 0.0285 mole) and triethylamine (3.97 ml, 0.0285 mole) in 50 ml. of ether. After stirring at 25° C. overnight, the solution was filtered and the filtrate was washed with 1.5% hydrochloric acid, 1.5% ammonium hydroxide and saturated sodium chloride solution. Concentration in vacuo afforded an oil which was chromatographed on silica gel eluting with ethyl acetate/cyclohexane (1:1) to yield ethyl N-trifluoroacetyl-N-(phenoxy(ethylthio)-phosphonomethyl)glycinate (1.5 g) as a clear oil, $N_D^{25} = 1.4969$.

Anal. Calc'd: C, 43.59; H, 4.63; S, 7.76; N, 3.39. Found: C, 43.71; H, 4.67; S, 7.64; N, 3.38.

EXAMPLE 19

A solution of ethanethiol (2.9 ml, 0.04 mole) and triethylamine (5.6 ml, 0.04 mole) in tetrahydrofuran (50 ml.) was added to n-butyl N-trifluoroacetyl-N-(dichlorophosphonomethyl)glycinate (14.3 g, 0.04 mole) in 250 ml. of ether at 0° C. After three hours, the solution was filtered and the filtrate was added to a cooled (0° C.) solution of isopropylamine (6.8 ml, 0.08 mole) in 50 ml. of tetrahydrofuran. After stirring for 16 hours at 25° C., the solution was filtered and the filtrate concentrated in vacuo. The residual oil was dissolved in 100 ml. methylene chloride and washed with 3% hydrochloric acid, 3% ammonium hydroxide and saturated sodium chloride solution. Concentration in vacuo afforded an oil which was chromatographed on silica gel eluting with ethyl acetate-cyclohexane (1:1) to afford n-butyl N-trifluoroacetyl-N-(isopropylamino(ethylthio)phosphonomethyl)glycinate (0.7 g) as a white solid, m.p. 64°–65° C.

Anal. Calc'd: C, 41.38; H, 6.45; N, 6.89. Found: C, 41.36; H, 6.48; N, 6.87.

EXAMPLE 20

A solution of diethylamine (5.0 ml, 0.05 mole) in 50 ml. of ether was added to ethyl N-trifluoroacetyl-N-(dichlorophosphonomethyl)glycinate (8.25 g, 0.025 mole) in 150 ml. of ether at 0° C. After three hours, the solution was filtered and the filtrate was treated with N-aminopiperidine (5.2 ml, 0.05 mole) in 50 ml. of ether. After stirring overnight, the mixture was filtered and the filtrate was washed with 0.3% aqueous hydrochloric acid, dried over sodium sulfate and concentrated in vacuo to afford an oil which was chromatographed on florosil eluting with methylene chloride. This afforded ethyl N-trifluoroacetyl-N-(diethylamino(N'-piperidinoamino)phosphonomethyl)glycinate (2.0 g) as a yellow wax, m.p. 63°–68° C.

Anal. Calc'd: C, 44.65; H, 7.03; N, 13.02. Found: C, 44.40; H, 6.99; N, 13.20.

EXAMPLE 21

A solution of n-butyl N-trifluoroacetyl-N-(dichlorophosphonomethyl)glycinate (14.3 g, 0.04 mole) in 250 ml. of ether was added slowly to a solution of morpholine (3.5 ml, 0.04 mole) and triethylamine (5.6 ml, 0.04 mole) in 100 ml. of ether. After three hours, the solution was filtered and the filtrate was added slowly to a cooled (0° C.) solution of p-chlorothiophenol (5.7 g, 0.04 mole) and triethylamine (5.6 ml, 0.04 mole) in 100 ml. of ether. After 16 hours at 25° C., the solution was filtered and the filtrate was concentrated in vacuo and the residual semi-solid was crystallized from ethyl acetate/cyclohexane (1/10). Recrystallization from hexane yielded butyl N-trifluoroacetyl-N-(morpholino(p-chlorothiophenoxy)phosphonomethyl)glycinate (2.1 g) as a white solid, m.p. 79.5°–81° C.

Anal. Calc'd: C, 44.15; H, 4.88; N, 5.42. Found: C, 43.48; H, 4.87; N, 5.65.

EXAMPLE 22

A solution of n-decyl N-trifluoroacetyl-N-(dichlorophosphonomethyl)glycinate (13.3 g, 0.03 mole) in 100 ml. of tetrahydrofuran was added to dibutylamine (5.0 ml, 0.03 mole) and triethylamine (4.2 ml, 0.03 mole) in 50 ml. of tetrahydrofuran. After three hours, the solution was filtered and the filtrate was added slowly to 4-bromo-m-thiocresol (5.8 ml, 0.03 mole) in 50 ml. of tetrahydrofuran. After stirring for 16 hours, the reaction mixture was filtered and the filtrate was concentrated in vacuo. The resulting oil was dissolved in methylene chloride, washed with 3% hydrochloric acid, 3% ammonium hydroxide and saturated aqueous sodium chloride. Concentration in vacuo afforded an oil which was chromatographed on silica gel eluting first with hexane, then with ethyl acetate to afford 2.1 g of n-decyl N-trifluoroacetyl-N-(dibutylamino(4'-bromo-3-methylthiophenoxy)phosphonomethyl)glycinate as an oil, $N_D^{22} = 1.5045$.

Anal. Calc'd: C, 51.35; H, 7.04; N, 3.99. Found: C, 51.49; H, 7.26; N, 3.98.

EXAMPLE 23

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | | | |
| --- | --- | --- | --- |
| A | Canada Thistle* | K | Barnyardgrass |
| B | Cocklebur | L | Soybean |
| C | Velvetleaf | M | Sugar Beet |
| D | Morningglory | N | Wheat |
| E | Lambsquarters | O | Rice |
| F | Smartweed | P | Sorghum |
| G | Yellow Nutsedge* | Q | Wild Buckwheat |
| H | Quackgrass* | R | Hemp Sesbania |
| I | Johnsongrass* | S | Panicum Spp |
| J | Downy Brome | T | Crabgrass |

*Established from vegetative propagules.

Table I

| Compound of Example No. | WAT | kg h | A | B | C | D | E | F | G | H | I | J | K |
| --- | --- | --- | --- | --- | --- | --- | --- | --- | --- | --- | --- | --- | --- |
| 1 | 4 | 11.2 | 0 | 3 | 2 | 2 | 3 | 0 | 1 | 1 | 2 | 2 | 2 |
| 1 | 4 | 5.6 | 0 | 2 | 1 | 1 | 3 | 0 | 2 | 1 | 3 | 1 | 2 |
| 2 | 4 | 11.2 | 2 | 2 | 1 | 2 | 4 | 1 | 2 | 3 | 3 | 4 | 4 |
| 2 | 4 | 5.6 | 1 | 2 | 1 | 1 | 2 | 1 | 2 | 2 | 1 | 2 | 2 |
| 3 | 4 | 11.2 | 1 | 3 | 2 | 3 | 4 | 2 | 3 | 1 | 3 | 1 | 2 |
| 3 | 4 | 5.6 | 1 | 2 | 1 | 2 | 2 | 1 | 1 | 1 | 2 | 0 | 2 |
| 4 | 4 | 11.2 | 1 | 2 | 3 | 3 | 1 | 1 | 1 | 1 | 2 | 1 | 3 |
| 4 | 4 | 5.6 | 0 | 1 | 1 | 1 | 1 | 0 | 0 | 0 | 1 | 1 | 1 |
| 5 | 4 | 11.2 | 2 | 2 | 3 | 3 | 2 | 1 | 0 | 2 | 1 | 1 | 3 |

Table I-continued

| Compound of Example No. | WAT | kg h | A | B | C | D | E | F | G | H | I | J | K |
|---|---|---|---|---|---|---|---|---|---|---|---|---|---|
| 6 | 4 | 11.2 | 1 | 2 | 1 | 2 | 4 | 2 | 1 | 1 | 0 | 0 | 2 |
| 6 | 4 | 5.6 | 0 | 1 | 1 | 1 | 4 | 0 | 0 | 0 | 0 | 0 | 1 |
| 7 | 4 | 11.2 | 2 | 3 | 2 | 3 | 4 | 2 | 2 | 1 | 1 | 1 | 4 |
| 7 | 4 | 5.6 | 4 | 4 | 2 | 3 | 4 | 4 | 3 | 1 | 3 | 1 | 3 |
| 8 | 4 | 11.2 | 2 | 4 | 3 | 2 | 4 | 3 | 2 | 1 | 2 | 3 | 3 |
| 8 | 4 | 5.6 | 2 | 4 | 3 | 2 | 4 | 2 | 2 | 2 | 2 | 2 | 3 |
| 9 | 4 | 11.2 | 2 | 4 | 3 | 3 | 4 | 3 | 2 | 1 | 1 | 2 | 4 |
| 10 | 4 | 11.2 | 2 | 3 | 1 | 2 | 1 | 4 | 2 | 1 | 2 | 1 | 4 |
| 10 | 4 | 5.6 | 1 | 2 | 1 | 2 | 1 | 0 | 2 | 0 | 1 | 0 | 2 |
| 11 | 2 | 11.2 | 0 | 0 | 0 | 0 | 0 | 2 | 0 | 0 | 0 | 0 | 0 |
| 12 | 4 | 11.2 | 2 | 4 | 3 | 2 | 3 | 3 | 3 | 2 | 3 | 3 | 3 |
| 12 | 4 | 5.6 | 1 | 3 | 4 | 2 | 2 | 3 | 2 | 3 | 3 | 4 | 3 |
| 13 | 4 | 11.2 | 3 | 4 | 4 | 3 | — | 3 | 3 | 3 | 3 | 3 | 3 |
| 13 | 4 | 5.6 | 4 | 4 | 3 | 3 | — | 1 | 3 | 2 | 3 | 3 | 3 |
| 15 | 2 | 11.2 | 0 | 0 | 0 | 1 | 0 | 0 | 0 | 0 | 0 | 0 | 1 |
| 16 | 4 | 11.2 | 2 | 4 | 3 | 3 | 3 | 3 | 1 | 2 | 1 | 1 | 3 |
| 17 | 4 | 11.2 | 2 | 3 | 3 | 2 | 1 | 1 | 2 | 1 | 2 | — | 3 |
| 17 | 4 | 5.6 | — | 3 | 2 | 2 | 4 | 4 | 2 | 2 | 3 | 2 | 4 |
| 18 | 4 | 11.2 | 0 | 1 | 1 | 1 | 1 | 0 | 1 | 2 | 0 | 0 | 2 |
| 19 | 4 | 11.2 | 1 | 2 | 1 | 2 | 1 | 2 | 1 | 1 | 0 | 2 | 2 |
| 19 | 4 | 5.6 | 1 | 2 | 1 | 2 | 2 | 0 | 1 | 3 | 0 | 2 | 2 |
| 20 | 4 | 11.2 | 2 | 4 | 2 | 2 | 1 | 1 | 2 | 1 | 2 | 0 | 4 |
| 20 | 4 | 5.6 | 2 | 2 | 1 | 2 | 3 | 1 | 2 | 0 | 1 | 0 | 3 |
| 21 | 4 | 11.2 | 0 | 1 | 1 | 2 | 4 | 0 | 2 | 0 | 1 | 2 | 2 |

Table II

| Compound of Example No. | WAT | kg h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 1 | 3 | 4 | 1 | 3 | 4 | 1 | 2 | 2 | 1 | 1 | 3 | 2 | 3 | 2 | 3 |
| 1 | 4 | 1.12 | 1 | 1 | 2 | 2 | 2 | 2 | 2 | 1 | 1 | 4 | — | 1 | 2 | 3 | 2 | 3 |
| 2 | 4 | 5.6 | 2 | 3 | 2 | 1 | 3 | 2 | 0 | 2 | 2 | 1 | 1 | 2 | 3 | 3 | 3 | 3 |
| 2 | 4 | 1.12 | 1 | 1 | 1 | 1 | 2 | 1 | 0 | 2 | 0 | 2 | 0 | 2 | 2 | 2 | 2 | 3 |
| 3 | 4 | 5.6 | 1 | 1 | 1 | 1 | 1 | 2 | 0 | 2 | 1 | 4 | 1 | 2 | 1 | 3 | 3 | 3 |
| 4 | 4 | 5.6 | 2 | 1 | 1 | 2 | 2 | 1 | 1 | 2 | 1 | 3 | 1 | 2 | 2 | 3 | 3 | 3 |
| 5 | 4 | 5.6 | 2 | 0 | 1 | 1 | 2 | 2 | 1 | 3 | 1 | 1 | 2 | 3 | 1 | 4 | 3 | 3 |
| 7 | 4 | 5.6 | 3 | 4 | 3 | 2 | 3 | 3 | 4 | 3 | — | 4 | 3 | 3 | 4 | 4 | 4 | 4 |
| 7 | 4 | 1.12 | 1 | 2 | 1 | 0 | 1 | 2 | 1 | 2 | 2 | 3 | 1 | 1 | 1 | 3 | 1 | 3 |
| 8 | 4 | 5.6 | 2 | 1 | 2 | 2 | 2 | 3 | 1 | 2 | 2 | 2 | 2 | 2 | 2 | 3 | 3 | 3 |
| 8 | 4 | 1.12 | 1 | 1 | 1 | 2 | 1 | 2 | 1 | 2 | 1 | 1 | 1 | 1 | 1 | 1 | 2 | 3 |
| 9 | 4 | 5.6 | 2 | 4 | 3 | 1 | 3 | 4 | 2 | 3 | 4 | 4 | 3 | 3 | 4 | 4 | 3 | 4 |
| 9 | 4 | 1.12 | 1 | 0 | 0 | 0 | 0 | 2 | 0 | 2 | 1 | 1 | 0 | 1 | 1 | 2 | 3 | 3 |
| 10 | 2 | 5.6 | 3 | 3 | 2 | 2 | 3 | 2 | 0 | 2 | 3 | 3 | 3 | 2 | 2 | 4 | 3 | 3 |
| 10 | 4 | 1.12 | 0 | 1 | 0 | 0 | 1 | 2 | 0 | 2 | 1 | 0 | 0 | 0 | 0 | 3 | 2 | 3 |
| 12 | 4 | 5.6 | 2 | 4 | 4 | 3 | 3 | 3 | 4 | 3 | 4 | — | 4 | 4 | 3 | 4 | 3 | 4 |
| 12 | 4 | 1.12 | 1 | 2 | 2 | 2 | 2 | 3 | 1 | 2 | 2 | — | 2 | 3 | 2 | 3 | 2 | 3 |
| 13 | 4 | 5.6 | 2 | 4 | 4 | 3 | 4 | 4 | 4 | 3 | 4 | 4 | 4 | 3 | 4 | 4 | 4 | 4 |
| 13 | 4 | 1.12 | 1 | 1 | 2 | 0 | 2 | 3 | 0 | 2 | 2 | 1 | — | 2 | 3 | 3 | 3 | 3 |
| 16 | 4 | 5.6 | 3 | 4 | 3 | 2 | 4 | 4 | 4 | 3 | 4 | 4 | 3 | 2 | 4 | 4 | 3 | 4 |
| 16 | 4 | 1.12 | 0 | 0 | 0 | 0 | 1 | 1 | 0 | 2 | 0 | — | 1 | 1 | 1 | 2 | 2 | 3 |
| 17 | 4 | 5.6 | 3 | 3 | 3 | 3 | 4 | 4 | 2 | 2 | 4 | 4 | 4 | 4 | 4 | 3 | 3 | 3 |
| 17 | 4 | 1.12 | 2 | 1 | 3 | 1 | 3 | 3 | 1 | 2 | 2 | 4 | 4 | 3 | 2 | 3 | 3 | 3 |

EXAMPLE 24

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in the following table.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

Table III

| Compound of Example No. | WAT | kg h | A | B | C | D | E | F | G | H | I | J | K |
|---|---|---|---|---|---|---|---|---|---|---|---|---|---|
| 1 | 2 | 11.2 | 1 | 0 | 0 | 0 | 0 | 0 | 0 | 2 | 0 | 1 | 1 |
| 2 | 2 | 11.2 | 3 | 0 | 1 | 1 | 2 | 0 | 0 | 3 | 2 | 1 | 1 |
| 3 | 2 | 11.2 | 0 | 0 | 0 | 0 | 0 | 0 | 0 | 1 | 0 | 0 | 0 |
| 4 | 2 | 11.2 | 0 | 0 | 1 | 0 | 0 | 0 | 0 | 1 | 0 | 0 | 0 |
| 6 | 2 | 11.2 | 0 | 0 | 3 | 0 | 0 | 0 | 0 | 0 | 0 | 0 | 0 |
| 7 | 2 | 11.2 | 3 | 0 | 0 | 1 | 0 | 0 | 1 | 0 | 0 | 0 | 0 |
| 8 | 2 | 11.2 | 3 | 0 | 1 | 1 | 1 | 0 | 1 | 3 | 0 | 0 | 2 |
| 9 | 2 | 11.2 | 2 | 0 | 0 | 0 | 0 | 0 | 1 | 0 | 0 | 0 | 0 |
| 10 | 2 | 11.2 | 2 | 0 | 0 | 0 | 0 | 0 | 0 | 0 | 0 | 0 | 0 |
| 11 | 2 | 11.2 | 0 | 0 | 0 | 0 | 3 | 0 | 0 | 0 | 0 | 0 | 0 |
| 12 | 4 | 11.2 | 3 | 1 | 1 | 2 | 2 | 0 | — | 2 | 0 | 2 | 3 |
| 13 | 2 | 11.2 | 0 | 0 | 0 | 0 | 1 | 0 | 1 | 3 | 0 | 0 | 0 |
| 14 | 2 | 11.2 | 0 | 1 | 0 | 1 | 1 | 1 | 0 | 3 | 2 | 0 | 3 |
| 16 | 2 | 11.2 | 3 | 0 | 0 | 0 | 0 | 0 | 1 | 2 | 0 | 0 | 0 |
| 17 | 4 | 11.2 | 3 | 1 | 1 | 2 | 3 | 2 | 3 | 3 | 1 | 3 | 1 |
| 18 | 2 | 11.2 | 2 | 0 | 0 | 1 | 1 | 0 | 3 | 3 | 1 | 0 | 0 |
| 19 | 2 | 11.2 | 2 | 1 | 1 | 2 | 2 | 0 | 1 | 3 | 0 | 1 | 3 |
| 21 | 2 | 11.2 | 3 | 0 | 0 | 2 | 1 | 0 | 3 | 2 | 0 | 1 | 0 |
| 22 | 2 | 11.2 | 0 | 0 | 0 | 0 | 0 | 0 | 0 | 0 | 2 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula $$CF_3-\overset{O}{\underset{\|}{C}}-N\overset{CH_2\overset{O}{\underset{\|}{C}}-OR}{\underset{CH_2-\overset{O}{\underset{\|}{P}}\overset{R_1}{\diagdown R_2}}{}}$$

wherein R is alkyl of from 1 to 10 carbon atoms or chlorinated $C_1-C_6$ alkyl, $R_1$ is a member of the group consisting of $C_1-C_6$ alkoxy, $C_1-C_6$ alkylthio, phenoxy, phenylthio, phenoxy or phenylthio substituted with one or two members of the group consisting of halo, cyano, nitro or trifluoromethyl, $C_1-C_6$ alkylamino, $C_1-C_6$ dialkylamino, morpholino and N-piperidinoamino and $R_2$ is a member of the group consisting of $C_1-C_6$ alkylthio, phenoxy, phenylthio, phenoxy or phenylthio substituted with one or two members of the group consisting of halo, cyano, nitro or trifluoromethyl, $C_1-C_6$ alkylamino, $C_1-C_6$ dialkylamino, alkenylamino, dialkenylamino, alkynylamino, dialkynylamino, wherein each alkenyl and alkynyl group contains up to six carbon atoms, morpholino and N-piperidinoamino with the proviso that $R_1$ and $R_2$ cannot represent the same group.

2. A compound of claim 1 wherein R is a $C_1-C_6$ alkyl group.

3. A compound of claim 2 wherein $R_1$ is $C_1-C_6$ alkoxy, phenoxy, phenylthio or $C_1-C_6$ alkylthio.

4. A compound of claim 3 wherein $R_2$ is $C_1-C_6$ alkylthio, $C_1-C_6$ alkylamino, phenylthio or N-piperidinoamino.

5. A compound of claim 4 which is ethyl N-trifluoroacetyl-N-(phenoxy(phenylthio)phosphonomethyl)glycinate.

6. A compound of claim 4 which is ethyl N-trifluoroacetyl-N-(methoxy(N-piperidinoamino)phosphonomethyl)glycinate.

7. A compound of claim 4 which is ethyl N-trifluoroacetyl-N-(phenylthio(isopropylamino)phosphonomethyl)glycinate.

8. A compound of claim 4 which is ethyl N-trifluoroacetyl-N-(phenoxy(N-piperidinoamino)phosphonomethyl)glycinate.

9. A compound of claim 4 which is ethyl N-trifluoroacetyl-N-(ethylthio(isopropylamino)phosphonomethyl)glycinate.

10. A herbicidal composition comprising an inert adjuvant and a herbicidally effective amount of a compound of the formula $$CF_3-\overset{O}{\underset{\|}{C}}-N\overset{CH_2\overset{O}{\underset{\|}{C}}-OR}{\underset{CH_2-\overset{O}{\underset{\|}{P}}\overset{R_1}{\diagdown R_2}}{}}$$

wherein R is alkyl of from 1 to 10 carbon atoms or chlorinated $C_1-C_6$ alkyl, $R_1$ is a member of the group consisting of $C_1-C_6$ alkoxy, $C_1-C_6$ alkylthio, phenoxy, phenylthio, phenoxy or phenylthio substituted with one or two members of the group consisting of halo, cyano, nitro or trifluoromethyl, $C_1-C_6$ alkylamino, $C_1-C_6$ dialkylamino, morpholino and N-piperidinoamino and $R_2$ is a member of the group consisting of $C_1-C_6$ alkylthio, phenoxy, phenylthio, phenoxy or phenylthio substituted with one or two members of the group consisting of halo, cyano, nitro or trifluoromethyl, $C_1-C_6$ alkylamino, $C_1-C_6$ dialkylamino, alkenylamino, dialkenylamino, alkynylamino, dialkynylamino, wherein each alkenyl and alkynyl group contains up to six carbon atoms, morpholino and N-piperidinoamino with the proviso that $R_1$ and $R_2$ cannot represent the same group.

11. A herbicidal composition of claim 10 wherein R is a $C_1-C_6$ alkyl group.

12. A herbicidal composition of claim 11 wherein $R_1$ is $C_1-C_6$ alkoxy, phenoxy, phenylthio or $C_1-C_6$ alkylthio.

13. A herbicidal composition of claim 12 wherein $R_2$ is $C_1-C_6$ alkylthio, $C_1-C_6$ alkylamino, phenylthio or N-piperidinoamino.

14. A herbicidal composition of claim 13 wherein the compound is ethyl N-trifluoroacetyl-N-(phenoxy(phenylthio)phosphonomethyl)glycinate.

15. A herbicidal composition of claim 13 wherein the compound is ethyl N-trifluoroacetyl-N-(methoxy(N-piperidinoamino)phosphonomethyl)glycinate.

16. A herbicidal composition of claim 13 wherein the compound is ethyl N-trifluoroacetyl-N-(phenylthio(isopropylamino)phosphonomethyl)glycinate.

17. A herbicidal composition of claim 13 wherein the compound is ethyl N-trifluoroacetyl-N-(phenoxy(N-piperidinoamino)phosphonomethyl)glycinate.

18. A herbicidal composition of claim 13 wherein the compound is ethyl N-trifluoroacetyl-N-(ethylthio(isopropylamino)phosphonomethyl)glycinate.

19. A herbicidal method which comprises contacting a plant or the plant growth medium with a herbicidally effective amount of a compound of the formula $$CF_3-\overset{O}{\underset{\|}{C}}-N\overset{CH_2\overset{O}{\underset{\|}{C}}-OR}{\underset{CH_2-\overset{O}{\underset{\|}{P}}\overset{R_1}{\diagdown R_2}}{}}$$

wherein R is alkyl of from 1 to 10 carbon atoms or chlorinated $C_1-C_6$ alkyl, R is a member of the group consisting of $C_1-C_6$ alkoxy, $C_1-C_6$ alkylthio, phenoxy, phenylthio, phenoxy or phenylthio substituted with one or two members of the group consisting of halo, cyano, nitro or trifluoromethyl, $C_1$–$C_6$ alkylamino, $C_1$–$C_6$ dialkylamino, morpholino and N-piperidinoamino and $R_2$ is a member of the group consisting of $C_1$–$C_6$ alkylthio, phenoxy, phenylthio, phenoxy or phenylthio substituted with one or two members of the group consisting of halo, cyano, nitro or trifluoromethyl, $C_1$–$C_6$ alkylamino, $C_1$–$C_6$ dialkylamino, alkenylamino, dialkenylamino, alkynylamino, dialkynylamino, wherein each alkenyl and alkynyl group contains up to six carbon atoms, morpholino and N-piperidinoamino with the proviso that $R_1$ and $R_2$ cannot represent the same group.

20. A herbicidal method of claim 19 wherein R is a $C_1$–$C_6$ alkyl group.

21. A herbicidal method of claim 20 wherein $R_1$ is $C_1$–$C_6$ alkoxy, phenoxy, phenylthio or $C_1$–$C_6$ alkylthio.

22. A herbicidal method of claim 21 wherein $R_2$ is $C_1$–$C_6$ alkylthio, $C_1$–$C_6$ alkylamino, phenylthio or N-piperidinoamino.

23. A herbicidal method of claim 22 wherein the compound is ethyl N-trifluoroacetyl-N-(phenoxy(phenylthio)phosphonomethyl)glycinate.

24. A herbicidal method of claim 22 wherein the compound is ethyl N-trifluoroacetyl-N-(methoxy(N-piperidinoamino)phosphonomethyl)glycinate.

25. A herbicidal method of claim 22 wherein the compound is ethyl N-trifluoroacetyl-N-(phenylthio(isopropylamino)phosphonomethyl)glycinate.

26. A herbicidal method of claim 22 wherein the compound is ethyl N-trifluoroacetyl-N-(phenoxy(N-piperidinoamino)phosphonomethyl)glycinate.

27. A herbicidal method of claim 22 wherein the compound is ethyl N-trifluoroacetyl-N-(ethylthio(isopropylamino)phosphonomethyl)glycinate.

* * * * *